United States Patent [19]

Singh

[11] 4,413,127

[45] Nov. 1, 1983

[54] PREPARATION OF 1,2-DIHYDRO-6-(LOWER ALKYL)-2-OXO-5-(PYRIDINYL)-NICOTINONITRILES

[75] Inventor: Baldev Singh, East Greenbush, N.Y.

[73] Assignee: Sterling Drug Inc., New York, N.Y.

[21] Appl. No.: 381,062

[22] Filed: May 24, 1982

[51] Int. Cl.$^3$ .......................................... C07D 213/64
[52] U.S. Cl. ................................................. 546/249
[58] Field of Search ........................................ 546/249

[56] References Cited

U.S. PATENT DOCUMENTS

| | | | |
|---|---|---|---|
| 2,824,121 | 2/1958 | Nicholl et al. | 260/484 |
| 4,223,149 | 9/1980 | Opalka, Jr. et al. | 546/257 |
| 4,276,293 | 6/1981 | Lesher et al. | 424/248.4 |
| 4,313,951 | 2/1982 | Lesher et al. | 424/263 |

OTHER PUBLICATIONS

Mezheritskii et al., Russian Chemical Reviews 42 (5), 392, 399-402 and 410 (1973).

*Primary Examiner*—Henry R. Jiles
*Assistant Examiner*—Bernard Dentz
*Attorney, Agent, or Firm*—Robert K. Bair; B. Woodrow Wyatt; Paul E. Dupont

[57] ABSTRACT

The invention resides in a process for preparing cardiotonically active 1,2-dihydro-6-(lower-alkyl)-2-oxo-5-(pyridinyl)nicotinonitriles (III) which comprises reacting a pyridinylmethyl lower-alkyl ketone (I) with tri-(lower-alkyl) orthoformate, acetic anhydride and acetic acid to produce 2-(lower-alkoxy)-1-(pyridinyl)ethenyl lower-alkyl ketone (II) and then reacting II with malononitrile in a lower-alkanol, where pyridinyl is 4- or 3-pyridinyl or 4- or 3-pyridinyl having one or two lower-alkyl substituents.

6 Claims, No Drawings

PREPARATION OF 1,2-DIHYDRO-6-(LOWER ALKYL)-2-OXO-5-(PYRIDINYL)NICOTINONITRILES

CROSS-REFERENCE TO RELATED APPLICATIONS

Singh copending U.S. patent application Ser. No. 303,178, filed Sept. 17, 1981 now U.S. Pat. No. 4,347,363, discloses and claims the process for preparing 1,2-dihydro-6-methyl-2-oxo-5-(pyridinyl)nicotinonitriles by reacting a pyridinylmethyl methyl ketone with ethoxymethylenemalononitrile.

Gelotte copending U.S. patent application Ser. No. 381,162, filed on even date herewith, discloses and claims the process for preparing 1,2-dihydro-6-(lower-alkyl)-2-oxo-5-(pyridinyl)nicotinonitriles by first reacting a pyridinylmethyl lower-alkyl ketone with tri-(lower-alkyl) orthoformate, acetic anhydride and acetic acid to produce 2-(lower-alkoxy)-1-(pyridinyl)ethenyl lower-alkyl ketone and then reacting said ketone, also claimed therein, with cyanoacetamide in the presence of a basic condensing agent and neutralizing the reaction mixture.

BACKGROUND OF THE INVENTION (a) Field of the Invention

This invention relates to a process for preparing cardiotonically active 1,2-dihydro-6-(lower-alkyl)-2-oxo-5-(pyridinyl)nicotinonitriles.

(b) Description of the Prior Art

Lesher and Philion U.S. Pat. No. 4,313,951, issued Feb. 2, 1982, based on application Ser. No. 198,461, filed Oct. 20, 1980, in turn, a continuation-in-part of its copending application Ser. No. 97,504, filed Nov. 26, 1979 and now abandoned, discloses, inter alia, the process for preparing a 1,2-dihydro-6-(lower-alkyl)-2-oxo-5-(pyridinyl)nicotinonitrile by first reacting a pyridinylmethyl lower-alkyl ketone with dimethylformamide di-(lower-alkyl) acetal to produce a 1-(pyridinyl)-2-(dimethylamino)ethenyl lower-alkyl ketone, then reacting said ketone with cyanoacetamide and acidifying the reaction mixture. This preparation also is shown in Lesher, Opalka and Page U.S. Pat. No. 4,276,293, issued June 30, 1981 and based on application Ser. No. 135,211, filed Mar. 28, 1980.

Opalka and Lesher U.S. Pat. No. 4,223,149, issued Sept. 16, 1980, discloses and claims the process for preparing a 1,2-dihydro-2-oxo-5-(pyridinyl)nicotinonitrile by reacting alpha-(pyridinyl)-beta-[di-(lower-alkyl)amino]-acrolein with malononitrile in a lower-alkanol.

Nicholl et al. U.S. Pat. No. 2,824,121, issued Feb. 18, 1958, discloses and claims an improved process for preparing "oxy alkylidene compounds" using a weakly acid compound as catalytic agent, e.g., zinc chloride, the process being particularly useful in preparing ethoxymethylene malonic diethyl ester by reaction of diethyl malonate and triethyl ortho-formate in the presence of acetic anhydride and catalytic amounts of zinc chloride.

Mezheritskii et al., Russian Chemical Reviews 42 (5), 392, 399–402 and 410 (1973), in a review article entitled "The Properties of Orthoesters and Their Applications in Organic Syntheses" has a section (pp. 399–402) re "VIII. Reactions of Orthoesters with Substances Containing An Active Methylene Group". Shown inter alia is the reaction of diethyl malonate with triethyl orthoformate by heating the reactants in the presence of an excess of acetic anhydride to produce diethyl ethoxymethylenemalonate.

SUMMARY OF THE INVENTION

The present invention resides in the process for preparing cardiotonically-active 1,2-dihydro-6-(lower-alkyl)-2-oxo-5-(pyridinyl)nicotinonitriles by first reacting a pyridinylmethyl lower-alkyl ketone with tri-(lower-alkyl) orthoformate, acetic anhydride and acetic acid to produce 2-(lower-alkoxy)-1-(pyridinyl)ethenyl lower-alkyl ketone and then reacting said ketone with malononitrile in a lower-alkanol. The resulting substituted-nicotinonitriles and their use as cardiotonic agents are disclosed in said Lesher and Philion U.S. Pat. No. 4,313,951.

DETAILED DESCRIPTION INCLUSIVE OF PREFERRED EMBODIMENTS

One aspect of the invention resides in the process which comprises reacting pyridinylmethyl lower-alkyl ketone of the formula

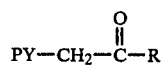

(I) with tri-(lower-alkyl) orthoformate, acetic anhydride and acetic acid to produce 2-(lower-alkoxy)-1-(pyridinyl)-ethenyl lower-alkyl ketone of formula II,

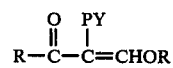

and reacting said ketone (II) with malononitrile in a lower-alkanol to produce 1,2-dihydro-6-R-2-oxo-5-PY-nicotinonitrile of formula III,

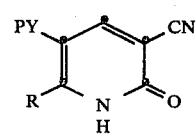

where R and R' are each lower-alkyl and PY is 4- or 3-pyridinyl or 4- or 3-pyridinyl having one or two lower-alkyl substituents. In a preferred embodiment 4(or 3)-pyridinylmethyl methyl(or ethyl) ketone is first reacted with triethyl or trimethyl orthoformate, acetic anhydride and acetic acid to produce 2-ethoxy(or methoxy)-1-(4- or 3-pyridinyl)ethenyl methyl(or ethyl) ketone and then said ketone is reacted with malononitrile in ethanol to produce 1,2-dihydro-6-methyl(or ethyl)-2-oxo-5-[4(or 3)-pyridinyl]nicotinonitrile. In a particularly preferred embodiment 4-pyridinylmethyl methyl ketone is first reacted with triethyl orthoformate, acetic anhydride and acetic acid to produce 2-ethoxy-1-(4-pyridinyl)ethenyl methyl ketone and then said ketone is refluxed with malononitrile in ethanol to produce 1,2-dihydro-6-methyl-2-oxo-5-(4-pyridinyl)-nicotinonitrile.

Another aspect of the invention resides in the second step of the above process, that is, the reaction of said ketone of formula II with malononitrile in a lower-alkanol to produce 1,2-dihydro-6-R-2-oxo-5-PY-nicotinonitrile of formula III. In a preferred embodiment, 2-ethoxy(or methoxy)-1-(4- or 3-pyridinyl)ethenyl methyl(or ethyl) ketone is reacted with malononitrile in ethanol to produce 1,2-dihydro-6-methyl(or ethyl)-5-[4(or 3)-pyridinyl]nicotinonitrile. In a particularly preferred embodiment, 2-ethoxy-1-(4-pyridinyl)ethenyl methyl ketone is refluxed with malononitrile in ethanol to produce 1,2-dihydro-6-methyl-2-oxo-5-(4-pyridinyl)nicotinonitrile.

Benefits of the instant process aspects over the Lesher and Philion prior art process for preparing 1,2-dihydro-6-(lower-alkyl)-5-(pyridinyl)nicotinonitriles inhere in the utilization of less expensive and more readily available starting materials and in the easier production of a pharmaceutically pure product. For example, triethyl orthoformate is much less expensive than dimethylformamide dimethyl acetal and, further, it is much more readily available in the large quantities needed for large-scale or commercial production.

The 1,2-dihydro-6-R-2-oxo-5-PY-nicotinonitriles of formula III produced by said process aspects of the invention and their use as cardiotonic agents are disclosed in said Lesher and Philion U.S. Pat. No. 4,313,951.

The term "lower-alkyl" as used herein means alkyl radicals having from one to four carbon atoms which can be arranged as straight or branched chains, illustrated by methyl, ethyl, n-propyl, isopropyl, n-butyl, 2-butyl or isobutyl.

The term "PY" as used herein means 4- or 3-pyridinyl or 4- or 3-pyridinyl having one or two "lower-alkyl" substituents, illustrated by 2-methyl-4-pyridinyl, 3-methyl-4-pyridinyl, 2-methyl-3-pyridinyl, 2,6-dimethyl-4-pyridinyl, 6-methyl-3-pyridinyl (alternatively named 2-methyl-5-pyridinyl), 2,3-dimethyl-4-pyridinyl, 2-ethyl-4-pyridinyl, 2-isopropyl-4-pyridinyl, 2-n-butyl-4-pyridinyl, 2,6-diethyl-4-pyridinyl, 2,6-diisopropyl-4-pyridinyl, and the like.

The term "lower-alkanol" as used herein means an alkanol having from one to four carbon atoms, illustrated by methanol, ethanol, n-propanol, isopropyl alcohol, n-butanol, and the like.

The molecular structures of the products produced by the process of the invention were assigned on the basis of evidence provided by infrared, nuclear magnetic resonance and mass spectra, by chromatographic mobilities, and by the correspondence of calculated and found values for the elementary analyses for representative examples.

The manner of making and using the instant invention will now be generally described so as to enable a person skilled in the art of chemistry to make and use the same, as follows:

The process of the invention is carried out by mixing tri-(lower-alkyl) orthoformate, preferably the triethyl or trimethylester, with (pyridinyl)methyl lower-alkyl ketone (I) and acetic anhydride in acetic acid as solvent. After an exothermic reaction subsides, the reaction mixture is stirred at ambient temperature until completion of the reaction, as determined by tlc analysis, to produce 1-(lower-alkoxy)-2-(pyridinyl)ethenyl lower-alkyl ketone (II). The reaction is run using an excess each of tri-(lower-alkyl)orthoformate, preferably about 1.3 to 1.7 mole per mole of ketone, and acetic anhydride, preferably about 2.0 to 3.0 mole per mole of ketone. The resulting intermediate ketone (II) can be used in the next step of the process without further purification or it can be isolated and further purified. The reaction of II with malononitrile to produce 1,2-dihydro-6-methyl-2-oxo-5-(pyridinyl)nicotinonitrile III is carried out by heating the reactants in a lower-alkanol at about 60° C. to 120° C., preferably about 75° C. to 100° C., particularly preferably in refluxing ethanol.

The following examples will further illustrate the invention without, however, limiting it thereto.

A. 1-(LOWER-ALKOXY)-2-(PYRIDINYL)ETHENYL METHYL KETONES

A-1. 1-Ethoxy-2-(4-pyridinyl)ethenyl Methyl Ketone, alternatively named 4-ethoxy-3-(4-pyridinyl)-3-buten-2-one-To a mixture containing 60 ml of triethyl orthoformate, 55 ml of acetic anhydride and 50 ml of acetic acid was added with stirring at room temperature over a 10 minute period 28.5 g of 1-(4-pyridinyl)propan-2-one whereupon an exothermic reaction took place raising the reaction temperature from 25° C. to 45° C. Stirring of the reaction mixture was continued while allowing the temperature to cool to room temperature and then continued overnight (about 16 hours). The reaction mixture was then concentrated on a rotary evaporator at about 70°–75° C. to yield 69.5 g of a red oil containing 1-ethoxy-2-(4-pyridinyl)ethenyl methyl ketone, which was used directly in the next step (Example B-1) without further purification.

A-2. 1-Methoxy-2-(4-pyridinyl)ethenyl methyl ketone, alternatively named 4-methoxy-3-(4-pyridinyl)-3-buten-2-one, 64.5 g, of a red oil containing said ketone, was obtained following the procedure described in Example A-1 using 38 ml of trimethyl orthoformate, 55 ml of acetic anhydride, 50 ml of acetic acid and 28.5 g of 1-(4-pyridinyl)propan-2-one. Said red oil was used directly in the next step without further purification.

Following the procedure described in Example A-1 but using in place of triethyl orthoformate a molar equivalent quantity of tri-n-propyl orthoformate, it is contemplated that the compound of Examples A-3 can be prepared.

A-3. 1-n-Propoxy-2-(4-pyridinyl)ethenyl methyl ketone.

Following the procedure described in Example A-1 but using in place of 1-(4-pyridinyl)propan-2-one a molar equivalent quantity of the appropriate (pyridinyl)methyl lower-alkyl ketone, it is contemplated that there can be obtained the corresponding 1-ethoxy-2-(pyridinyl)ethenyl lower-alkyl ketones of Examples 4 through 9.

A-4. 1-Ethoxy-2-(3-pyridinyl)ethenyl methyl ketone, using 1-(3-pyridinyl)propan-2-one.

A-5. 1-Ethoxy-2-(2-methyl-4-pyridinyl)ethenyl methyl ketone, using 1-(2-methyl-4-pyridinyl)propan-2-one.

A-6. 1-Ethoxy-2-(2-ethyl-4-pyridinyl)ethenyl methyl ketone, using 1-(2-ethyl-4-pyridinyl)propan-2-one.

A-7. 1-Ethoxy-2-(2,6-dimethyl-4-pyridinyl)ethenyl methyl ketone, using 1-(2,6-dimethyl-4-pyridinyl)propan-2-one.

A-8. 1-Ethoxy-2-(4-pyridinyl)ethenyl ethyl ketone, using 1-(4-pyridinyl)butan-2-one.

A-9. 1-Ethoxy-2-(4-pyridinyl)ethenyl n-propyl ketone, using 1-(4-pyridinyl)penta-2-one.

B. 1,2-DIHYDRO-6-(LOWER-ALKYL)-2-OXO-5-(PYRIDINYL)NICOTINONITRILES

B-1. 1,2-Dihydro-6-methyl-2-oxo-5-(4-pyridinyl)-nicotinonitrile-A 69.5 g portion of 1-ethoxy-2-(4-pyridinyl)ethenyl methyl ketone (Example A-1) was dissolved in 300 ml of ethanol and to the solution was added 13.2 g of malononitrile. The resulting mixture was refluxed for 5 hours, crystals starting to separate after about 30 minutes of refluxing. The reaction mixture was allowed to cool to room temperature; and, the precipitate of fine needles was filtered, washed with ethanol and dried in a vacuum oven at 90° C. to yield 25.4 g of 1,2-dihydro-6-methyl-2-oxo-5-(4-pyridinyl)-nicotinonitrile, m.p. >300° C. Concentration of the mother liquor provided another 2.1 g of product, m.p. >300° C.

B-2. 1,2-Dihydro-6-methyl-2-oxo-5-4-pyridinyl)-nicotinonitrile, 15.3 g, m.p. >300° C., also was prepared following the procedure described in Example B-1 using 64.5 g of 1-methoxy-2-(4-pyridinyl)ethenyl methyl ketone (Example A-2), 13.2 g of malononitrile and 300 ml. of ethanol. An additional 6.2 g of the product was obtained from the mother liquor after concentrating it to dryness on a rotary evaporator and crystallizing the residual material from ethanol, m.p. >300° C.

Following the procedure described in Example B-1 but using in place of 1-ethoxy-2-(4-pyridinyl)ethenyl methyl ketone molar equivalent quantity of the appropriate 1-alkoxy-2-(pyridinyl)ethenyl lower-alkyl ketone, it is contemplated that there can be obtained the corresponding 1,2-dihydro-6-(lower-alkyl)-2-oxo-5-(pyridinyl)nicotinonitriles of Examples B-3 through B-8.

B-3. 1,2-Dihydro-6-methyl-2-oxo-5-(3-pyridinyl)-nicotinonitrile, using 1-ethoxy-2-(3-pyridinyl)ethenyl methyl ketone.

B-4. 1,2-Dihydro-6-methyl-5-(2-methyl-4-pyridinyl)-2-oxonicotinonitrile, using 1-ethoxy-2-(2-methyl-4-pyridinyl)ethenyl methyl ketone.

B-5. 5-(2-Ethyl-4-pyridinyl)-1,2-dihydro-6-methyl-2-oxonicotinonitrile, using 1-ethoxy-2-(2-ethyl-4-pyridinyl)ethenyl methyl ketone.

B-6. 1,2-Dihydro-6-methyl-5-(2,6-dimethyl-4-pyridinyl)-2-oxonicotinonitrile, using 1-ethoxy-2-(2,6-dimethyl-4-pyridinyl)ethenyl methyl ketone.

B-7. 6-Ethyl-1,2-dihydro-5-(4-pyridinyl)-2-oxonicotinonitrile, using 1-ethoxy-2-(4-pyridinyl)ethenyl ethyl ketone.

B-8. 1,2-Dihydro-6-n-propyl-5-(4-pyridinyl)-2-oxonicotinonitrile, using 1-ethoxy-2-(4-pyridinyl)ethenyl n-propyl ketone.

I claim:

1. The process which comprises reacting pyridinyl-methyl lower-alkyl ketone of the formula

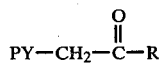

with tri(lower-alkyl) orthoformate, acetic anhydride and acetic acid to produce 2-(lower-alkoxy)-1-(pyridinyl)-ethenyl lower-alkyl ketone of the formula

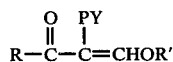

and reacting said ketone with malononitrile in a lower-alkanol to produce 1,2-dihydro-6-R-2-oxo-5-PY-nicotinonitrile of the formula

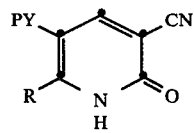

where R and R' are each lower-alkyl and PY is 4- or 3-pyridinyl or 4- or 3-pyridinyl having one or two lower-alkyl substituents.

2. The process according to claim 1 where 4 (or 3)-pyridinylmethyl methyl(or ethyl) ketone is first reacted with triethyl or trimethyl orthoformate, acetic anhydride and acetic acid to produce 2-(ethoxy or methoxy)-1-(4- or 3-pyridinyl)ethenyl methyl(or ethyl) ketone and then reacting said ketone with malononitrile in ethanol to produce 1,2-dihydro-6-(methyl or ethyl)-2-oxo-5-[4(or 3)-pyridinyl]nicotinonitrile.

3. The process according to claim 2 where 4-pyridinylmethyl methyl ketone is first reacted with triethyl orthoformate, acetic anhydride and acetic acid to produce 2-ethoxy-1-(4-pyridinyl)ethenyl methyl ketone and then refluxing said ketone with malononitrile in ethanol to produce 1,2-dihydro-6-methyl-2-oxo-5-(4-pyridinyl)nicotinonitrile.

4. The process which comprises reacting 2-(lower-alkoxy)-1-(pyridinyl)-ethenyl lower-alkyl ketone of the formula

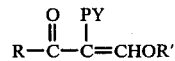

with malononitrile to produce 1,2-dihydro-6-R-2-oxo-5-PY-nicotinonitrile of the formula

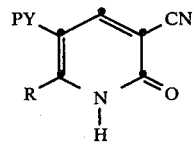

where R and R' are each lower-alkyl and PY is 4- or 3-pyridinyl or 4- or 3-pyridinyl having one or two lower-alkyl substituents.

5. The process according to claim 4 where 2-(ethoxy or methoxy)-1-(4- or 3-pyridinyl)ethenyl methyl(or ethyl) ketone is reacted with malononitrile in ethanol to produce 1,2-dihydro-6-(methyl or ethyl)-2-oxo-5-[4(or 3)-pyridinyl]nicotinonitrile.

6. The process according to claim 4 where 2-ethoxy-1-(4-pyridinyl)ethenyl methyl ketone is refluxed with malononitrile in ethanol to produce 1,2-dihydro-6-methyl-2-oxo-5-(4-pyridinyl)nicotinonitrile.

* * * * *

UNITED STATES PATENT AND TRADEMARK OFFICE
CERTIFICATE OF CORRECTION

PATENT NO. : 4,413,127

DATED : November 1, 1983

INVENTOR(S) : Baldev Singh

It is certified that error appears in the above-identified patent and that said Letters Patent is hereby corrected as shown below:

The numerals "1" and "2", defining the positions of the alkoxy and pyridinyl substituents, respectively, in the names of the ketones of formula II should be interchanged at the following places of the printed patent:

Column 3, line 58

Column 4, lines 5, 7, 20, 23, 36, 42, 45, 47, 50, 52, 55, 57 and 62

Column 5, lines 10, 18, 20, 26, 30, 33, 36, 39 and 42.

Signed and Sealed this

Twenty-fourth Day of February, 1987

Attest:

DONALD J. QUIGG

Attesting Officer

Commissioner of Patents and Trademarks